United States Patent
Fogwill et al.

(10) Patent No.: US 9,719,971 B2
(45) Date of Patent: Aug. 1, 2017

(54) MICROFLUIDIC FLAME IONIZATION DETECTOR

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US); Geoff Gerhardt, Millbury, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/483,389

(22) Filed: Sep. 11, 2014

(65) Prior Publication Data

US 2015/0078962 A1    Mar. 19, 2015

Related U.S. Application Data

(60) Provisional application No. 61/877,548, filed on Sep. 13, 2013.

(51) Int. Cl.
*G01N 30/68* (2006.01)
*G01N 30/60* (2006.01)

(52) U.S. Cl.
CPC ......... *G01N 30/68* (2013.01); *G01N 30/6095* (2013.01)

(58) Field of Classification Search
CPC ...................................................... G01N 30/68
USPC ........................................................... 422/54
See application file for complete search history.

(56) References Cited

U.S. PATENT DOCUMENTS

| 2004/0043479 | A1* | 3/2004 | Briscoe et al. ............ 435/288.5 |
| 2005/0287033 | A1 | 12/2005 | Thurbide |
| 2014/0035593 | A1 | 2/2014 | Kuipers |

FOREIGN PATENT DOCUMENTS

| WO | 2009036854 A1 | 3/2009 |
| WO | 2012055835 A1 | 5/2012 |

OTHER PUBLICATIONS

Hayward, T.C. et al., "Carbon response characteristics of a microflame ionization detector," Talanta, Apr. 2007, vol. 73, 583-588.
Dziurdzia, B. et al., "A ceramic mini system for the detection of hydrocarbon radicals," Meas. Sci. Technol., Apr. 2008, vol. 19, 055206-055211.
Search and Examination Report for GB1416137.6, dated Jun. 11, 2015.
Hayward, T.C. et al., "Novel on-column and inverted operating modes of a microcounter-current flame ionization detector," J. Chromatogr. A, Feb. 2008, vol. 1200, 2-7.

* cited by examiner

*Primary Examiner* — Paul Hyun
(74) *Attorney, Agent, or Firm* — McCarter & English, LLP; Deborah M. Vernon

(57) ABSTRACT

The present disclosure relates to a microfluidic flame ionization detector for use in small scale separations, such as, for example, microfluidic gas chromatography and microfluidic carbon dioxide based fluid chromatography. In some arrangements, the microfluidic counter-current flame ionization detector employs a non-parallel arrangement for the introduction of combustion gases into the combustion chamber. In other arrangements, the detector housing is configured to incorporate at least one of the detector electrodes within the housing using electrically isolating fittings.

20 Claims, 12 Drawing Sheets

Microfluidic FID housing assembly

MICROFLUIDIC FLAME IONIZATION DETECTOR

CROSS-REFERENCE TO RELATED APPLICATIONS

This application claims priority to U.S. Provisional Application No. 61/877,548 filed Sep. 13, 2013, which is incorporated herein by reference in its entirety.

FIELD OF THE TECHNOLOGY

The present disclosure relates to a microfluidic flame ionization detector for use in small scale separations, such as microfluidic chromatographic separations. In some arrangements, the microfluidic flame ionization detector employs a non-parallel arrangement for the introduction of combustion gases into the combustion chamber. In other arrangements, the detector housing is configured to incorporate at least one of the detector electrodes within the housing using electrically isolating fittings.

BACKGROUND

Separation technology continues to evolve from bulk separation systems, such as packed gas chromatography and conventional FID, to smaller separations systems, such as microfluidic chromatographic systems. Miniaturized separation systems have many advantages including significantly reduced combustion gas requirements as well as reduced sample volume and mass requirements. For example, a microfluidic detector may use up to five times less hydrogen gas and up to twenty times less air versus conventional gas chromatography-FID.

The development of small scale separation platforms requires the development of correspondingly compatible detection systems. For example, the development of a microfluidic separation system requires the development of similar micro detectors. Micro flame detectors have been developed and demonstrated for adaption with conventional gas chromatography instrumentation and capillary GC columns. For example, U.S. 2005/0287033 describes a microfluidic counter-current flame detector for use in conventional gas chromatography. The detector is adapted to a standard GC instrument and is capable of detecting various analytes separated using a capillary GC column. See also T. C. Hayward, K. B. Thurbide/Talanta 73 (2007) 583-588. Similarly, a compact separation system has been developed which includes a capillary column manufactured into an alumina substrate and combined with a microfluidic flame detector on a single piece of ceramic. See B. Dziurdia et al., Meas. Sci. Technol. 19 (2008).

SUMMARY

The present disclosure relates to a microfluidic flame ionization detector for use in small scale separations, such as, for example, microfluidic gas chromatography and microfluidic carbon dioxide based fluid chromatography. In some arrangements, the microfluidic flame ionization detector employs a non-parallel arrangement for the introduction of combustion gases into the combustion chamber. The non-parallel arrangement generates a spatially constrained flame and improves the response of the detector relative to other small-scale FID arrangements. In other arrangements, the detector housing is configured to incorporate one or more of the detector electrodes as part of the housing.

In one embodiment, the present disclosure relates to a microfluidic flame ionization detector, comprising a housing, a combustion chamber contained within the housing, a microfluidic oxygen inlet contained within the housing and in fluid communication with the combustion chamber, a microfluidic effluent and hydrogen inlet contained within the housing and in fluid communication with the combustion chamber, a polarizer electrode, the polarizer electrode held at a first potential, and a collector electrode, the collector electrode held at a second potential, wherein the second potential is greater than the first potential, wherein a portion of the housing functions as at least one of the polarizer electrode or collector electrode. The portion of the housing functioning as at least one of the electrodes includes an electrically isolated base electrode. In some embodiments, the oxygen inlet and the effluent and hydrogen inlet may be disposed in a non-parallel arrangement relative to one another.

In another embodiment, the present disclosure relates to a microfluidic separation system having a sample injector, a separation device in fluid communication and downstream of the injector, and a microfluidic flame ionization detector, as described herein, in fluid communication with and downstream of the separation device. The microfluidic separation system may be a gas chromatographic separation system or a carbon dioxide based separation system.

The embodiments of the present disclosure further include the following features. The housing may include at least two portions which function individually as the polarizer electrode or the collector electrode. Both portions can be electrically isolated base electrodes. Each electrically isolated base electrode should include a non-conducting material, such as ceramic, polymer or combinations thereof. The non-conducting material may be in the form of an electrically isolating fitting. The oxygen inlet and the effluent and hydrogen inlet may be disposed at an angle of about 150° to about 210°, relative to each other, at or leading into the combustion chamber. The inlets may also be in a substantially opposing relationship at or leading into the combustion chamber (i.e., disposed at an angle of about 180°).

The second potential is greater than the first potential (e.g., held at a greater electric potential). In some embodiments, the second potential may be a positive potential and the first potential may be a less positive, a neutral or a negative potential. Alternatively, the first potential may be a negative potential and the second potential may be a less negative, a neutral or a positive potential. The potential difference between the second and first potentials is about 10 V to about 500 V.

The design of the microfluidic FID makes it compatible for the incorporation into a microfluidic platform which combines both a separation column and the detector in a single microfluidic device. By incorporating both components in a separation system (e.g., GC-FID platform, SFC-FID platform) the system may be miniaturized and simplified. The detector's compact configuration integrates the electrodes (e.g., the polarizer and collector electrodes) into the detector body to provide structural support for the detector while remaining electrically isolated. The integrated system eliminates potential operator error in reliably making the performance-critical fluidic connections between components. Finally, the size and low system requirements (e.g., sample size, mobile phase, flame gas) of the single microfluidic device allow for the potential use outside of a laboratory setting (e.g., remote testing or field-portability).

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION

Figure 1A:
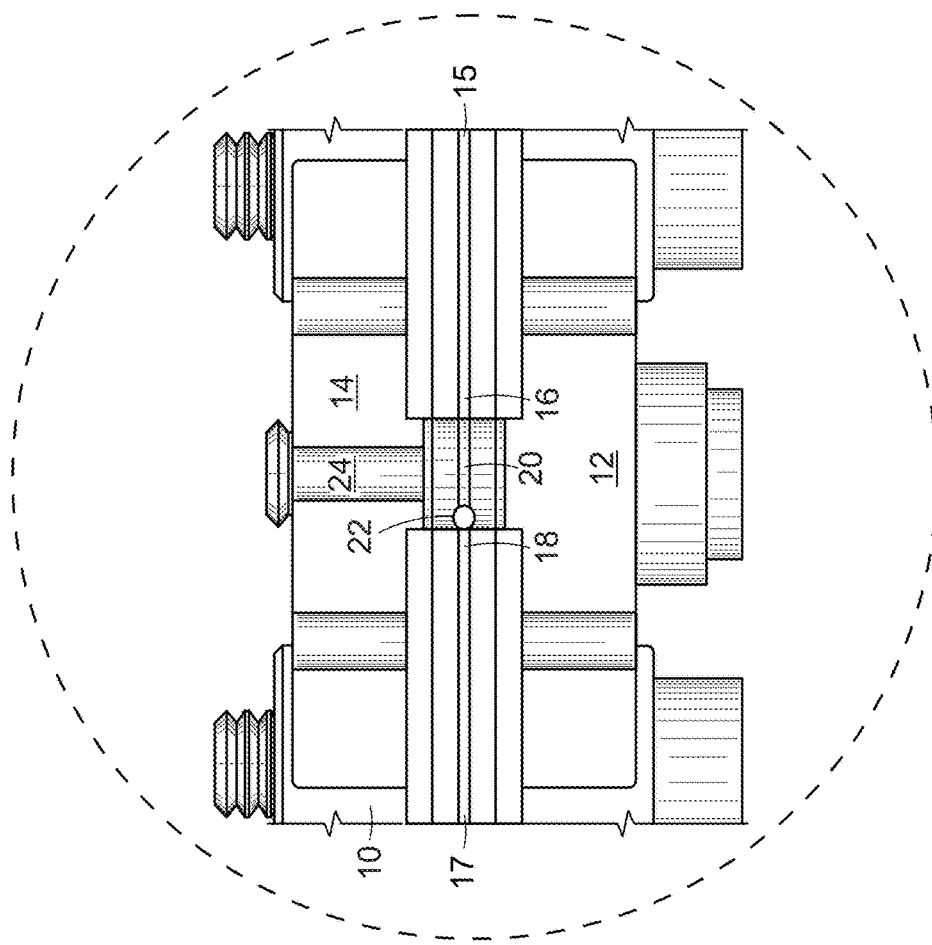
FIG. 1A shows additional details of the embodiment including a housing (10), a polarizer electrode (12), a collector electrode (14), an oxygen channel (15), an oxygen channel inlet (16), a column effluent and hydrogen channel (17), a column effluent and hydrogen channel inlet (18), a combustion chamber (20), the FID flame (22) and an exhaust port (24).

The microfluidic FID of the present disclosure is designed to be compact, efficient and produce a stable, sensitive flame. Its size is reduced to a scale appropriate for implementation in a microfluidic chromatographic system. For example, the detector minimizes the consumption of flame gases. A conventional gas chromatography FID consumes about 40 mL/min of hydrogen and about 450 mL/min of air. In some embodiments, the microfluidic FID consumes only about 10 mL/min of hydrogen and about 20 mL/min of oxygen. The present disclosure describes the design of a microfluidic FID for operation in a microfluidic chromatographic system. The applicable microfluidic chromatographic systems include gas chromatographic and carbon dioxide based chromatographic systems (e.g., microfluidic GC platforms, capillary-scale carbon dioxide based chromatography systems, solvating GC, and capillary-scale SFC separations).

The implementation of the microfluidic FID to a microfluidic chromatographic system also eliminates the need for a transfer line between the column and the detector. The elimination of a transfer line reduces the system volume, which may reduce band broadening and improve chromatographic performance.

As used herein, the term "microfluidic chromatographic system" refers to a chromatographic or separation system involving the manipulation of extremely small volumes of fluids (e.g., liquid or gas). The system is capable of flowing (i.e., pumping, delivering or transporting) fluid through the chromatographic column at a flow rates as low as about 1 µL/min or less. The system is also capable of separating analyte(s) from a minute quantity of sample fluid.

The detector platform may take many shapes. In one embodiment, the detector platform has a generally planar shape. As used herein, the term "planar" refers to a general shape of the detector platform configured as substantially containing the detector components in the same plane (e.g., wafer, glass slide).

In one embodiment, the present disclosure relates to a microfluidic flame ionization detector, comprising a housing, a combustion chamber contained within the housing, a microfluidic oxygen inlet contained within the housing and in fluid communication with the combustion chamber, a microfluidic effluent and hydrogen inlet contained within the housing and in fluid communication with the combustion chamber, a polarizer electrode, the polarizer electrode held at a first potential, and a collector electrode, the collector electrode held at a second potential, wherein the second potential is greater than the first potential, wherein a portion of the housing functions as at least one of the polarizer electrode or collector electrode. The portion of the housing functioning as at least of the electrodes includes an electrically isolated base electrode. The housing may include at least two portions which function individually as the polarizer electrode or the collector electrode. Both portions include electrically isolated base electrodes. The electrically isolated base electrode includes a non-conducting material, such as ceramic, polymer or combinations thereof. The non-conducting material may be in the form of an electrically isolating fitting. The oxygen inlet and the effluent and hydrogen inlet can be disposed in a non-parallel arrangement relative to one another.

In another embodiment, the present disclosure relates to a microfluidic flame ionization detector having a housing, wherein the housing has a planar shape. The planar shaped housing contains a microfluidic oxygen inlet for delivering oxygen to a combustion chamber and a microfluidic effluent and hydrogen inlet for delivering column effluent and hydrogen to the combustion chamber. The combustion chamber is contained within the planar shaped housing and is in fluid communication with the oxygen inlet, the effluent and hydrogen inlet, and an exhaust port. The planar shaped housing also contains a polarizer electrode, the polarizer electrode held at a first potential, and a collector electrode which is electrically isolated from the polarizer electrode, the collector electrode held at a second potential. The collector electrode is electrically insulated from the polarizer electrode to prevent shorting the detector. The second potential is greater than the first potential. The oxygen inlet and the effluent and hydrogen inlet can be disposed in a non-parallel arrangement relative to one another.

Figure 1:
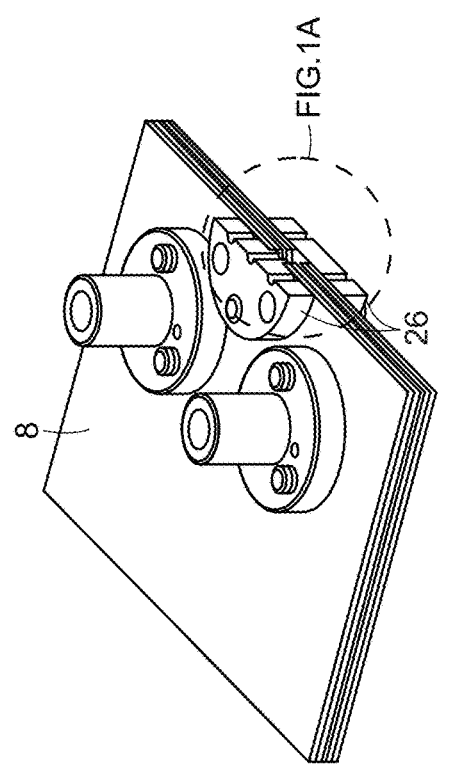
FIG. 1 shows one embodiment of the present disclosure having a microfluidic substrate (8) and electrically isolated fittings which function as the base electrodes (26).

FIG. 1 (and FIG. 1A) shows an embodiment of the present disclosure having a housing (10). The housing (10) may be made using a material capable of containing and operating an FID having at least a polarizer electrode (12) and a collector electrode (14). The microfluidic substrate (8), including the housing (10), the polarizer electrode (12), the collector electrode (14), etc. should not contain carbon or carbon containing materials at or near the vicinity of the combustion chamber (20) and/or the FID flame (22). The detector responds to carbon and the presence of extraneous carbon may interfere with the detection of organic substances burned in the FID flame (22). Preferably, these components are free or substantially free of carbon or carbon containing materials. The microfluidic platform, including the housing (10), the polarizer electrode (12), the collector electrode (14) may be composed of metallic, ceramic, carbon-free polymeric substrates, or combinations thereof.

In some embodiments, the housing (10) includes stainless steel, diffusion bonded titanium, low temperature co-fired ceramic (LTCC), high temperature co-fired ceramic (HTCC), or combinations thereof. In some embodiments, the electrodes may be encased within layers of ceramic (co-fired). In other embodiments, the polarizer electrode (12) and the collector electrode (14) may individually comprise stainless steel, titanium, tungsten, palladium, platinum or combinations thereof.

The detector has a polarizer electrode (12) and a collector electrode (14). The polarizer electrode (12) may be arranged in a known configuration or made using a known material for use in an FID. A portion of the housing (10) may function as the polarizer electrode (12). This portion of the housing (10) may be electrically isolated and offset from the collector electrode (14) at the combustion chamber (20). The polarizer electrode (12) is substantially held at a first potential.

The collector electrode (14) may also be arranged in a known configuration or made using a known material for use in an FID. A portion of the housing (10) may function as the collector electrode (14). This portion of the housing (10) may be electrically isolated and offset from the polarizer electrode (12) at the combustion chamber (20). Preferably, the polarizer electrode (12) and the collector electrode (14) are offset and electrically isolated from each other. The polarizer electrode (12) and a collector electrode (14) may be electrically isolated from each other using non-conductive fasteners (e.g., PEEK screws) and/or layers (e.g., PEEK washers). For example, an non-conductive layer may be used and a portion of which may extend into an electrode through-hole. A non-conductive screw may then be passed through the layer and thread into the opposite electrode. In some embodiments, the polarizer electrode (12) and the collector electrode (14) may both be a portion of the housing (10). One or both may be contained in an electrically isolated fitting (26) adapted, attached or connected to the housing (10). In one embodiment, the collector electrode (14) is contained in an electrically isolated fitting (26) adapted, attached or connected to the housing. The collector electrode (14) is substantially held at a second potential. The electrically isolating modified fittings (26) may by composed of ceramic, polymer or combinations thereof. In some embodiments, the fittings are carbon-free. In one embodiment, the electrically isolating fitting (26) includes ceramic. In another embodiment, the electrically isolating fitting (26) includes a polymer (e.g., polymer layer). The polymer may include polyether ether ketone (PEEK) or polyimide.

The second potential of the collector electrode (14) is greater than the first potential of the polarizer electrode (12). The electric field between the polarizer electrode (12) and the collector electrode (14) accelerates the positive ions generated by chemical ionization of organic substances burned in the FID flame (22) from the polarizer electrode (12) to the collector electrode (14). The concentration of the organic substances within the sample is determined by changes in the detected ion current.

The second potential of the collector electrode (14) is greater, or more positive, than the first potential of the polarizer electrode (12). The difference potential difference between the polarizer electrode (12) and the collector electrode (14) may range from about 10 V to about 500 V. Preferably, the difference in potential is about 20 V to about 300 V. For example, the polarizer electrode (12) may be held at ground and the collector electrode (14) may be held at between +20 to +300 V. In one embodiment, the second potential may be a positive potential and the first potential may be a less positive, a negative potential or a neutral potential. In other embodiment, the first potential may be a negative potential and the second potential may be a less negative, a positive potential or a neutral potential.

The microfluidic channels (or traces) are shown as (15) and (17). The path of these channels, independent of each other, may vary depending on the specific design of the device. At times, the paths of these channels, relative to each other, can run parallel (0 degree difference), counter-current (e.g., 180 degree difference) or any variation in between. The inlets are shown as (16) and (18). The inlets are the ends of the channels that are in fluid communication with the combustion chamber (20). In one embodiment, the oxygen supply into the combustion chamber (20) is provided via the microfluidic oxygen inlet (16), and the column effluent and hydrogen supply are provided via the microfluidic effluent and hydrogen inlet (18). In alternate embodiments, the column effluent can be provided to the combustion chamber via an additional separate inlet, in combination with a make-up gas, or combinations thereof.

Figure 2:
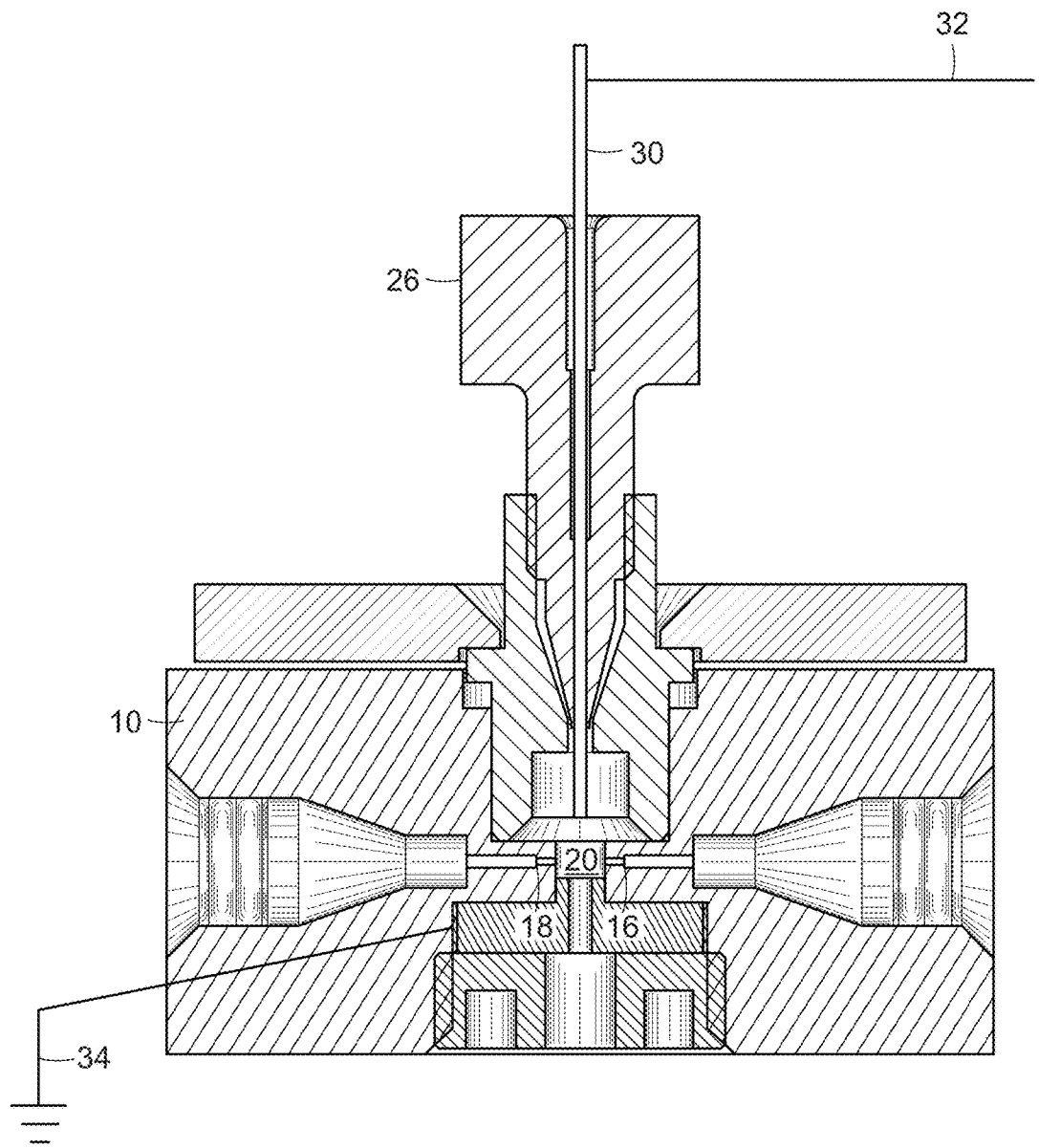
FIG. 2 is another embodiment of the present disclosure showing a stainless steel prototype of a microfluidic counter-current FID including a housing (e.g., stainless steel) (10), an oxygen channel inlet (16), a column effluent and hydrogen channel inlet (18), a combustion chamber (20), an electrically isolated fitting (26), a collector electrode extension (30), an electrical connection to the electrometer (32), wherein the housing functions also as a polarizer electrode (34).

FIG. 2 shows a prototype design of the microfluidic counter-current FID in a metallic substrate as described in Example 1. In this embodiment, the combustion chamber (20) was constructed out of stainless steel. The hydrogen/column effluent enters the chamber (20) through a microfluidic effluent and hydrogen inlet (18) which is about 180° opposed from the oxygen flow which enters the chamber through a microfluidic oxygen inlet (16). The lower portion of the housing (10) of the FID prototype is held at ground potential (34) to function as the FID polarizer electrode. A tungsten wire acts as the collector electrode (30) which is electrically isolated from this portion of the housing (10) and is positioned near the flame. The collector electrode (30) is connected to an electrical connection (32) to the electrometer. The collector electrode (30) and electrical connection (32) may be a known extension and connection compatible with flame ionization detectors.

The housing and polarizer electrode (10) can also be configured to have an inlet for oxygen to be delivered to the combustion chamber (20). The microfluidic oxygen channel (15) and/or inlet (16) can be within the planar body of the detector platform. The shape and dimensions of the channel and/or inlet can be a size or configuration capable of delivering a sufficient amount, or flow, of oxygen to the combustion chamber (20). The microfluidic oxygen channel

(15) and inlet (16) can be configured to accommodate fluid flow rates ranging from about 5 mL/min to about 500 mL/min.

In one embodiment, the microfluidic oxygen channel (15) and inlet (16) are configured to accommodate, and the detector is configured to consume, an oxygen flow rate of less than about 100 mL/min. Preferably, the microfluidic oxygen channel (15) and inlet (16) are configured to accommodate, and the detector is configured to consume, an oxygen flow rate of less than about 20 mL/min.

The microfluidic oxygen channel (15) and inlet (16) can also be configured to accommodate, and the detector is configured to consume, an air flow rate of less than about 500 mL/min. Preferably, the microfluidic oxygen channel (15) and inlet (16) are configured to accommodate, and the detector is configured to consume, an air flow rate of less than about 100 mL/min.

The polarizer electrode (12) can also be configured to have an inlet for the separation effluent and hydrogen to be delivered to the combustion chamber (20). The microfluidic effluent and hydrogen channel (17) and/or inlet (18) can be configured within the planar body of the detector platform. The shape and dimensions of the channel and inlet can be a size or configuration capable of delivering a sufficient amount, or flow, of effluent and hydrogen to the combustion chamber (20) and minimizing flow disruption and band broadening effects. In some embodiments, the microfluidic effluent and hydrogen channel (17) and inlet (18) should have substantially the same dimensions as the separation column or channel used to effect the separation (e.g., gas chromatographic systems). In other embodiments, the microfluidic effluent and hydrogen channel (17) and/or inlet (18) has substantially smaller dimensions as the separation column or channel used to effect the separation (e.g., carbon dioxide based chromatographic systems). For example, the microfluidic effluent and hydrogen channel (17) and inlet (18) can have a 40 µm i.d. and the separation column may have a 500 µm i.d. The microfluidic effluent and hydrogen channel (17) and inlet (18) can be configured to accommodate fluid flow rates ranging from about 5 mL/min to about 100 mL/min.

In some embodiments, the microfluidic effluent and hydrogen are pre-mixed to ensure proper operation of a diffusion flame. A diffusion flame involves a hydrogen-rich environment on the inside and an oxidant-rich environment on the outside of the flame. A diffusion flame allows for cracking of a hydrocarbon to methane in the inner part of the flame and partial oxidation of methane to CHO+ in the outside of the flame. In other embodiments, a makeup gas is pre-mixed with the column effluent alone or the column effluent and hydrogen. Pre-mixing the column effluent (alone or with hydrogen) with a make-up gas may result in better sensitivity of the detector depending on the specific conditions of the separation (e.g., the sample, the effluent, the combustion gas flows and the design of the detector).

In one embodiment, the microfluidic effluent and hydrogen channel (17) and inlet (18) is configured to accommodate, and the detector is configured to consume, a hydrogen flow rate of less than about 50 mL/min. Preferably, the microfluidic effluent and hydrogen channel (17) and inlet (18) is configured to accommodate, and the detector is configured to consume, a hydrogen flow rate of less than about 10 mL/min. Changes in the detector response may occur due to differences in the column effluent gas type (e.g., He, $CO_2$, $N_2$). Also, the column effluent flow rate correlates to a range of hydrogen flow rates for a stable and consistent detector response. If the column effluent flow rate increases or decreases, the hydrogen flow may require a corresponding adjustment to maintain a stable and consistent detector response.

Conventional flame ionization detectors configure the FID gas flow, e.g. oxygen, air, hydrogen, nitrogen, and the column effluent flow, in a parallel arrangement. For example, the separation column carrying the effluent is typically surrounded by a larger sleeve carrying the FID gases. The flows of the effluent and the FID gases are parallel leading up to and at the combustion chamber and FID flame. While the figures show the counter-current arrangement, the advantages of the present disclosure can also be obtained with FID gas flow configured in a parallel arrangement. In these embodiments, the microfluidic oxygen inlet (16) and the microfluidic effluent and hydrogen inlet (18) are disposed in a parallel arrangement (not shown).

In other embodiments, the microfluidic oxygen inlet (16) and the microfluidic effluent and hydrogen inlet (18) are disposed in a non-parallel arrangement relative to one another. FIGS. 1 and 2 show embodiments wherein microfluidic oxygen inlet (16) and the microfluidic effluent and hydrogen inlet (18) are directed about 180° (degrees) relative to each other. This counter-current arrangement of the FID combustion gases helps to spatially constrain the flame and improve response in the microfluidic counter-current FID relative to other small-scale FID arrangements. In one embodiment, the microfluidic oxygen inlet (16) and the microfluidic effluent and hydrogen inlet (18) can be disposed in a substantially opposing relationship at the combustion chamber. The microfluidic oxygen inlet (16) and the microfluidic effluent and hydrogen inlet (18) may be disposed at an angle of about 150° to about 210° at the combustion chamber. Preferably, they may be disposed at an angle of about 170° to 190° at the combustion chamber. More preferably, they may be disposed at an angle of substantially about 180° at the combustion chamber.

The combustion chamber (20) can be arranged in a configuration or made using a material for use in an FID. In some embodiments, the combustion chamber (20) may also be within the planar body of the detector platform and bracketed by the polarizer electrode (12) and the collector electrode (14). The combustion chamber (20) is in fluid communication with the microfluidic oxygen inlet (16) and the microfluidic effluent and hydrogen inlet (18), as well as the exhaust port (24).

The FID flame (22) is contained within the combustion chamber (20). The flame has a small volume, preferably less than about 1 microliter (or less than about 0.1 cm×0.1 cm×0.1 cm). In some embodiments, the FID flame (22) can be situated closer to, or adjacent to, the microfluidic oxygen inlet (16) into the combustion chamber (20). The flame may be lit by accessing the combustion chamber (20) via the exhaust port (24). In general, once lit the FID flame (22) remains stable for hours.

Figure 3:
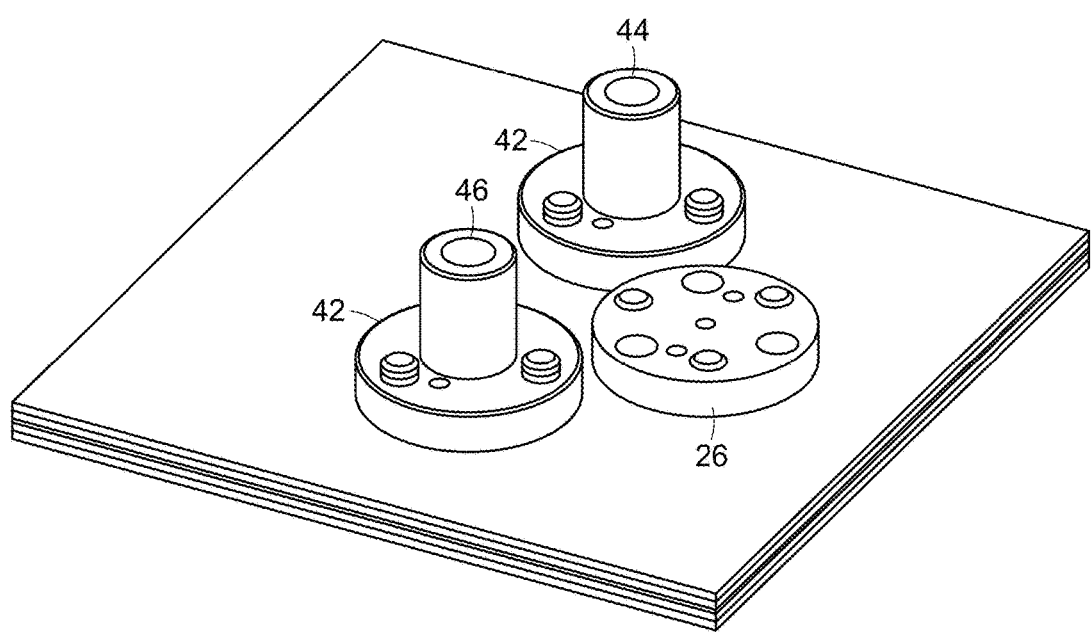
FIG. 3 is another embodiment of the present disclosure showing exterior fluid connections into the microfluidic counter-current FID including bolt on capillary fittings (42), an oxygen inlet port (44), a column effluent and hydrogen inlet port (46) and an electrically isolated fitting (26).
Figure 4:
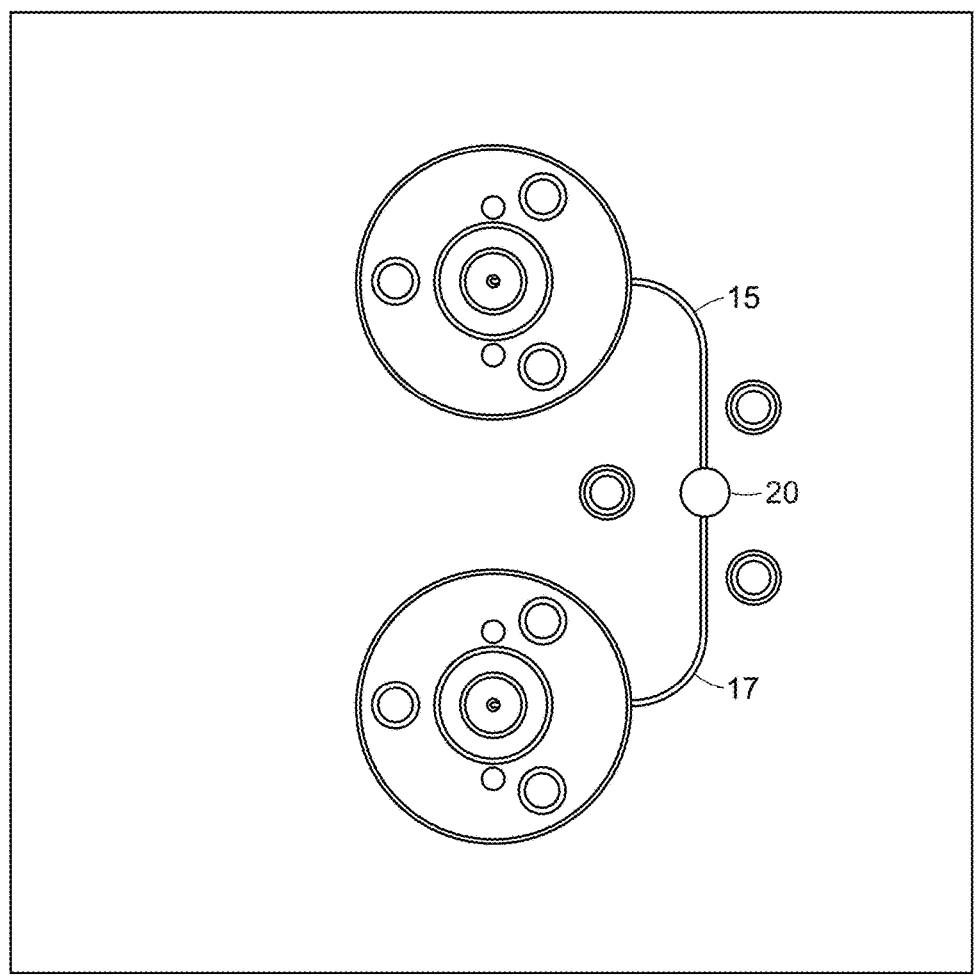
FIG. 4 is another embodiment of the present disclosure showing a diagram of microfluidic channels in a microfluidic counter-current FID including an oxygen channel (15), a column effluent and hydrogen channel (17) and a combustion chamber (20).

FIG. 3 depicts another embodiment showing external fluidic connections to the microfluidic platform. As shown, a pair of capillary tubing adapters (42) provide the fluidic connections for the column effluent and hydrogen inlet port (46) as well as the oxygen inlet port (44). Two modified fitting base discs (26, only one shown) made of stainless steel are electrically isolated from each other and function as the collector and polarizer electrodes. FIG. 4 shows an exemplary configuration of the microfluidic channels, microfluidic oxygen channel (15) and the microfluidic effluent and hydrogen channel (17) that carry at least one of the column effluent and combustion gases from the external fluidic connections to the combustion chamber (20).

Figure 5:
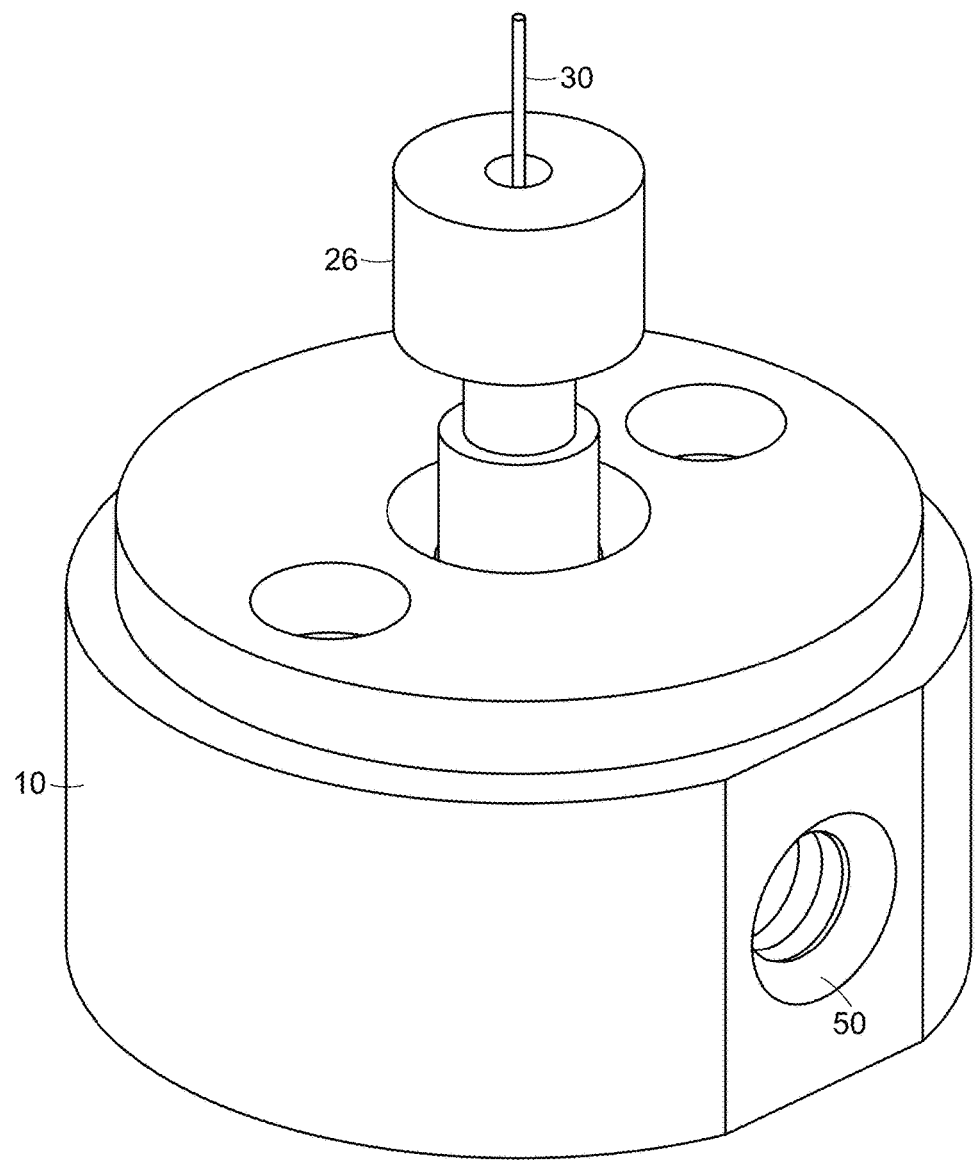
FIG. 5 is another embodiment of the present disclosure showing the exterior of a stainless steel prototype of a microfluidic counter-current FID including a stainless steel housing (10), an electrically isolated fitting (26), a collector electrode extension (30) and one of the two inlet ports for the oxygen or column effluent/hydrogen channel (50).

FIG. 5 shows another exemplary configuration of the exterior of a stainless steel prototype of a microfluidic counter-current FID including an electrically isolated fitting (26), a stainless steel housing (10), the collector electrode extension (30) and one of the two inlet ports for the oxygen or column effluent/hydrogen channels (50). In other embodiments, the microfluidic counter-current FID can have separate column effluent, hydrogen, and makeup flow channels. Two or more of these channels may join together at or near the combustion chamber.

The compact size and design of the detector of the present disclosure makes it compatible with microfluidic chromatographic systems. In one embodiment, the present disclosure relates to a microfluidic chromatographic system comprising a sample injector; a separation device in fluid communication and downstream of the injector; and a microfluidic flame ionization detector as described herein in fluid communication with and downstream of the separation device. Non-limiting examples of the microfluidic chromatographic system include microfluidic gas chromatographic systems and microfluidic carbon dioxide based chromatographic systems.

Such small scale separations can also be incorporated into a field portable, hand held separation device. The detector can be incorporated into a field portable, hand held separation device capable of performing microfluidic scale separations. The microfluidic detector can also function as a free-standing microfluidic device containing only the FID or as an integrated microfluidic platform housing both a separation column and the FID. These systems can be adapted for use in a wide variety of applications, including for microfluidic GC, microfluidic supercritical fluid chromatography (SFC), microfluidic carbon dioxide based chromatography systems or as an independent detector connected to the end of a conventional SFC or GC column.

The disclosures of all cited references including publications, patents, and patent applications are expressly incorporated herein by reference in their entirety. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

A microfluidic counter-current flame ionization detector was manufactured. FIGS. 2 and 5 show the components of the detector. All of the components were made of stainless steel with the exception of the collector electrode and the electrically isolating fitting. The collector electrode (30) was made of tungsten. The electrically isolating fitting (26) was made of PEEK. The oxidant channel (15) and inlet (16), and the column effluent/hydrogen channel (17) and inlet (18) were all 200 µm in diameter. The combustion chamber (20) had an inner diameter of 1.6 mm.

A test separation was performed using the microfluidic counter-current flame ionization detector. A commercially available gas chromatograph equipped with an autosampler and a split/splitless inlet was used for sample introduction and column heating. The inlet was held at 250° C. and employed a 50:1 split ratio. The separation was performed on a 30 m by 0.32 mm i.d. wall coated open tubular column with a 0.25 µm thick DB-5 (5% phenyl, 95% dimethyl polysiloxane) stationary phase. The column was heated isothermally to 180° C. A helium carrier gas was employed at 1.5 mL/min. The column was connected to the microfluidic counter-current flame ionization detector. The detector was located outside of the GC oven. A heated transfer line was connected to the column to heat the column and transfer line residing outside of the GC oven. The heated transfer line was held at 180° C.

The microfluidic counter-current flame ionization detector housing (10), or body, functioned as the polarizer electrode (34). The housing (10) was held at ground potential. The tungsten wire functioned as the collector electrode (30) and was held at +180 V. The housing (10) of the microfluidic counter-current flame ionization detector was heated and held at 180° C. to prevent analyte condensation.

Figure 6:
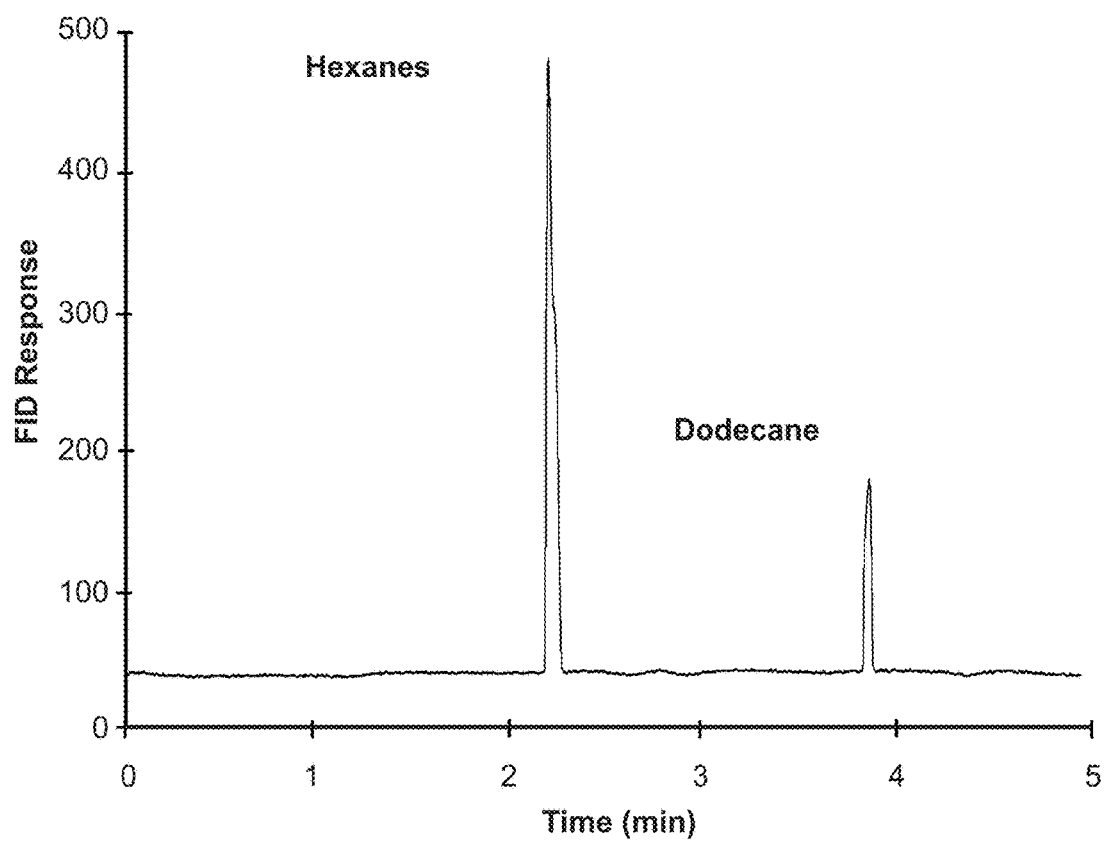
FIG. 6 is a chromatogram from a separation performed using the embodiment of the microfluidic counter-current FID described in Example 1.

The flame was supported by 40 mL/min of oxygen and 13 mL/min of hydrogen. The hydrogen was pre-mixed with the column effluent before entering the housing (10). An example chromatogram is shown in FIG. 6. FIG. 6 shows a separation of a 20 µg/mL dodecane test sample dissolved in hexanes.

Example 2

A second microfluidic counter-current flame ionization detector was manufactured. FIGS. 1, 3 and 4 show the exemplary components of the second detector. All of the components were made of low temperature co-fired ceramic with the exception of the tubing connections and electrodes. The tubing connections and electrodes (e.g., polarizer electrode (12) and collector electrode (14)) were made of stainless steel. Both the polarizer electrode (12) and collector electrode (14) make up portions of the housing. Each electrode had a length of copper wire brazed on for electrical connections. The polarizer electrode (12) and collector electrode (14) were electrically isolated from each other by small PEEK insulators. The oxidant channel (15) and inlet (16), and the column effluent/hydrogen channel (17) and inlet (18) all had a square profiles with the cross-sectional equivalent area of a 100 µm i.d. round tube. The combustion chamber had an inner diameter of was 1.6 mm.

A test injection was performed using the microfluidic counter-current flame ionization detector. A commercially available gas chromatograph equipped with a split/splitless inlet was used for sample introduction and column heating. Manual 1 µL injections were made. A short length of 0.1 mm i.d. capillary column was employed. The column was connected to the detector using a transfer line held at room temperature. A hydrogen carrier gas was employed at 10 mL/min.

Figure 7:
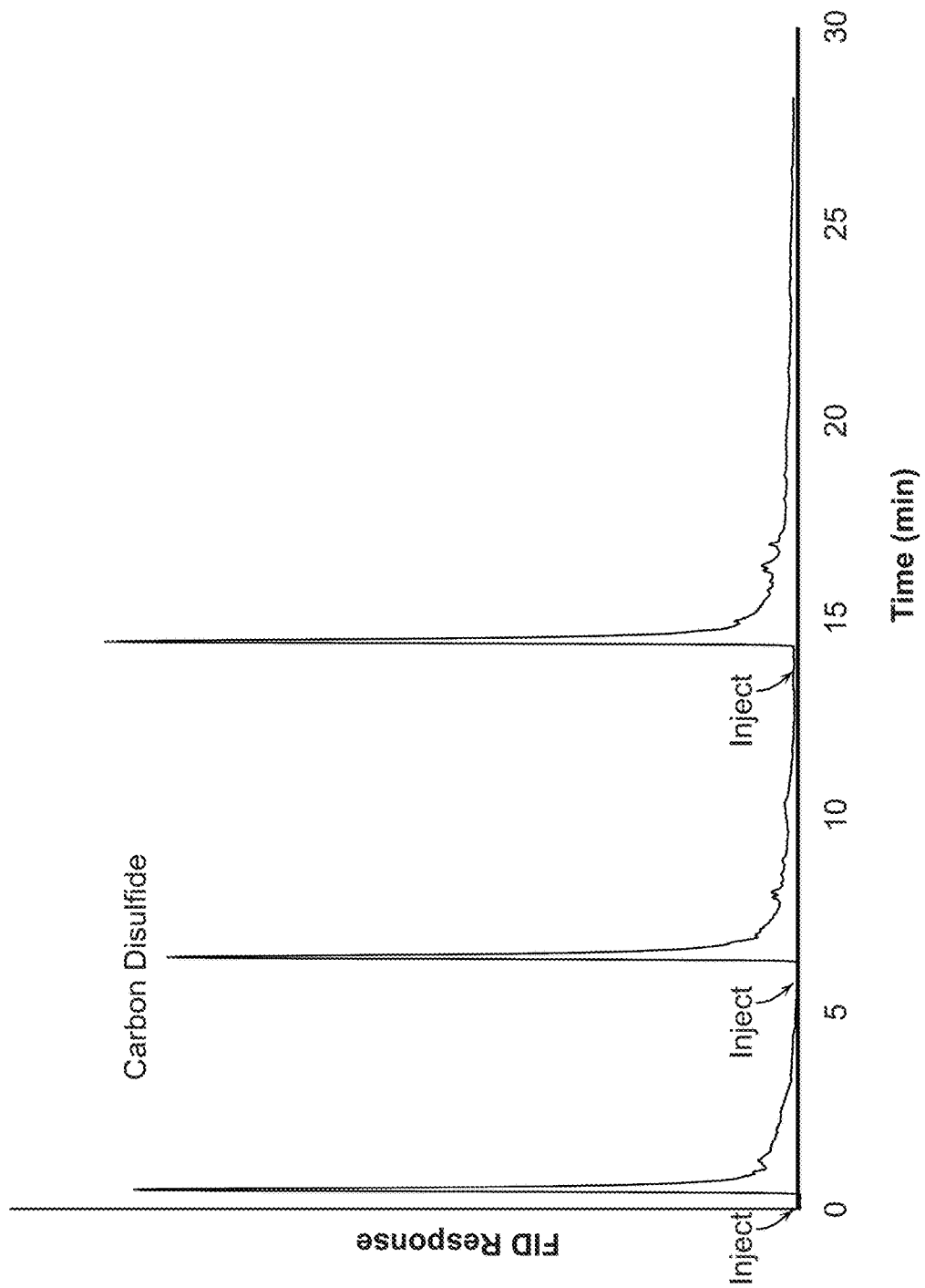
FIG. 7 is a chromatogram from a separation performed using the embodiment of the microfluidic counter-current FID described in Example 2.

One of the stainless steel electrodes functioned as the polarizer electrode (12) and was held at ground potential. The second stainless steel electrode functioned as the collector electrode (14) and was held at +300 V. The 10 mL/min hydrogen carrier gas flow provided the fuel for the flame and 6 mL/min oxygen was introduced through the oxidant channel to support the flame. An example chromatogram for multiple injections of neat carbon disulfide is shown in FIG. 7.

Example 3

A third microfluidic counter-current flame ionization detector was manufactured. FIGS. 8-11 show illustrations of the detector. The Figures are labeled consistent with Examples 1 and 2, and the specification. The microfluidic device was made from either titanium, low temperature co-fired ceramic or high temperature co-fired ceramic. The perimeter dimensions of the microfluidic substrate (8) were about 12.7 mm by 50.8 mm by 2.4 mm thick. Variations of the materials used and the dimensions can be made depending on the specific application of the detector.

The gas fittings (42) were made from stainless steel and designed to accommodate 360 micrometer outer diameter fused silica tubing. The electrodes (12, 14, 26) were also made from stainless steel. The electrodes were isolated from each other and the base microfluidic device using small ceramic isolators. During development, polyimide gaskets (i.e., polymer gaskets) were used in place of the ceramic isolators. The polyimide gaskets did not perform as well as the ceramic isolators. The polyimide gaskets overheated and contributed to the FID signal.

Figure 8:
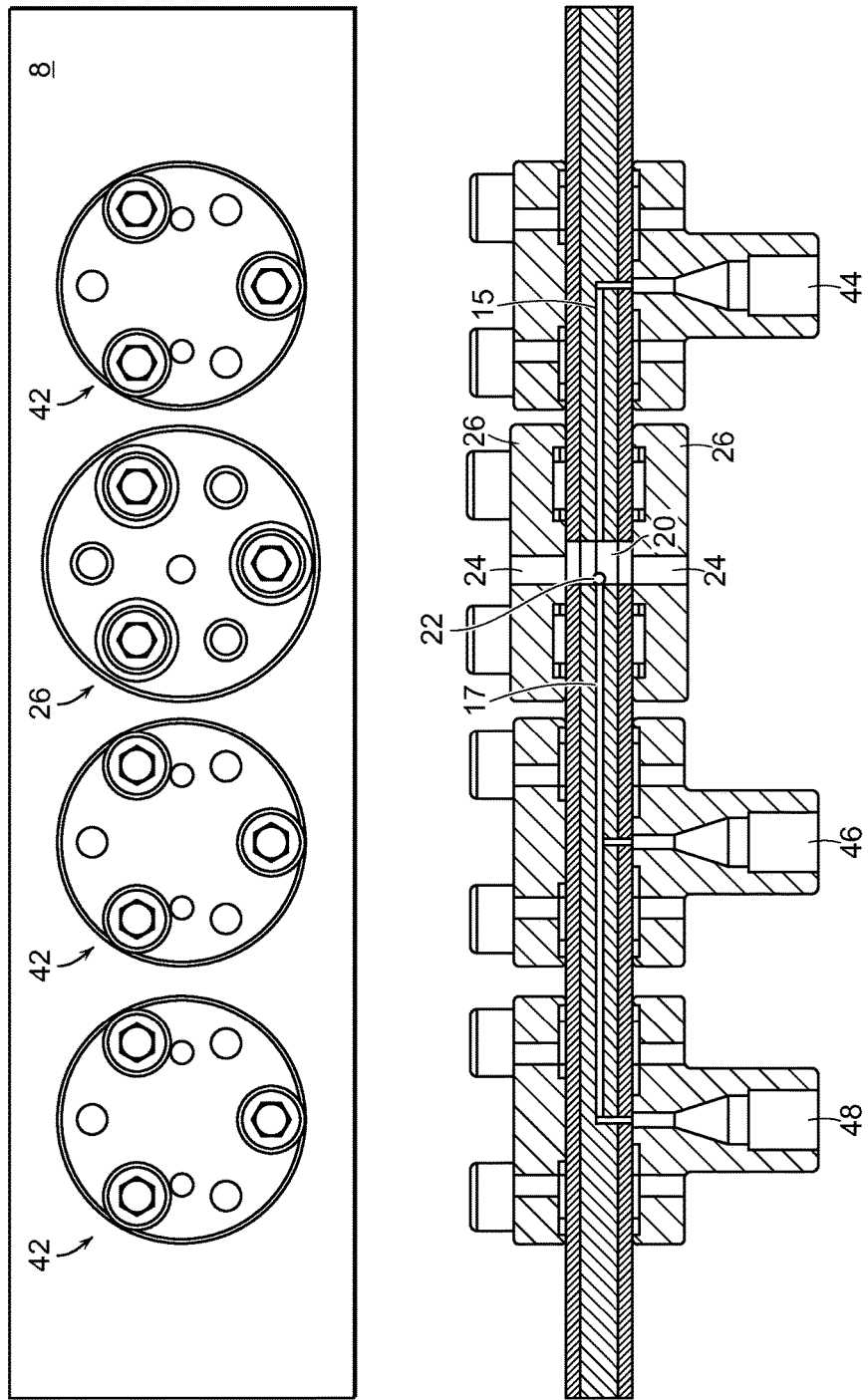
FIGS. 8 and 9 are another embodiment of the present disclosure showing the microfluidic counter-current FID described in Example 3
Figure 9:
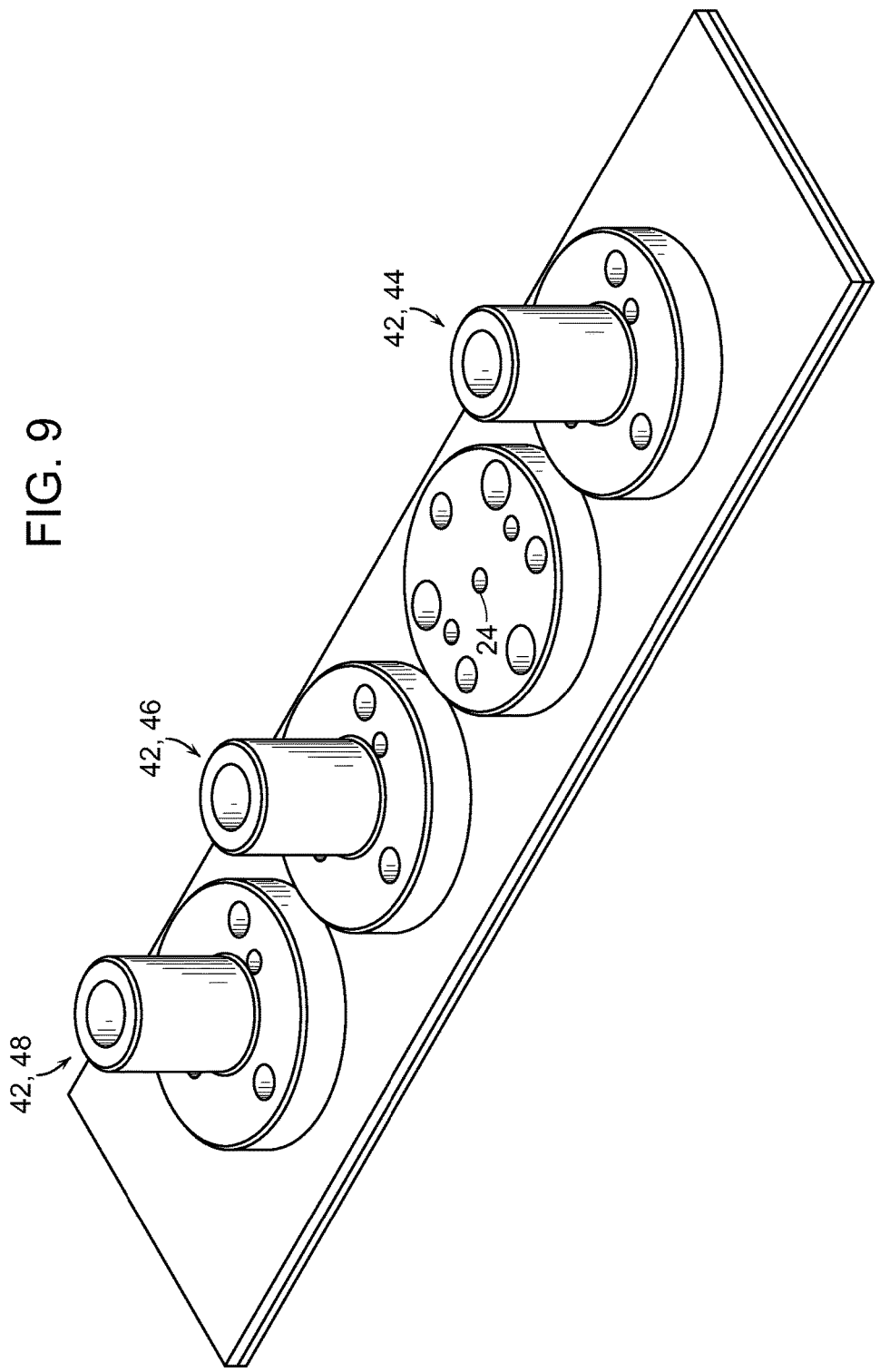
Figure 10:
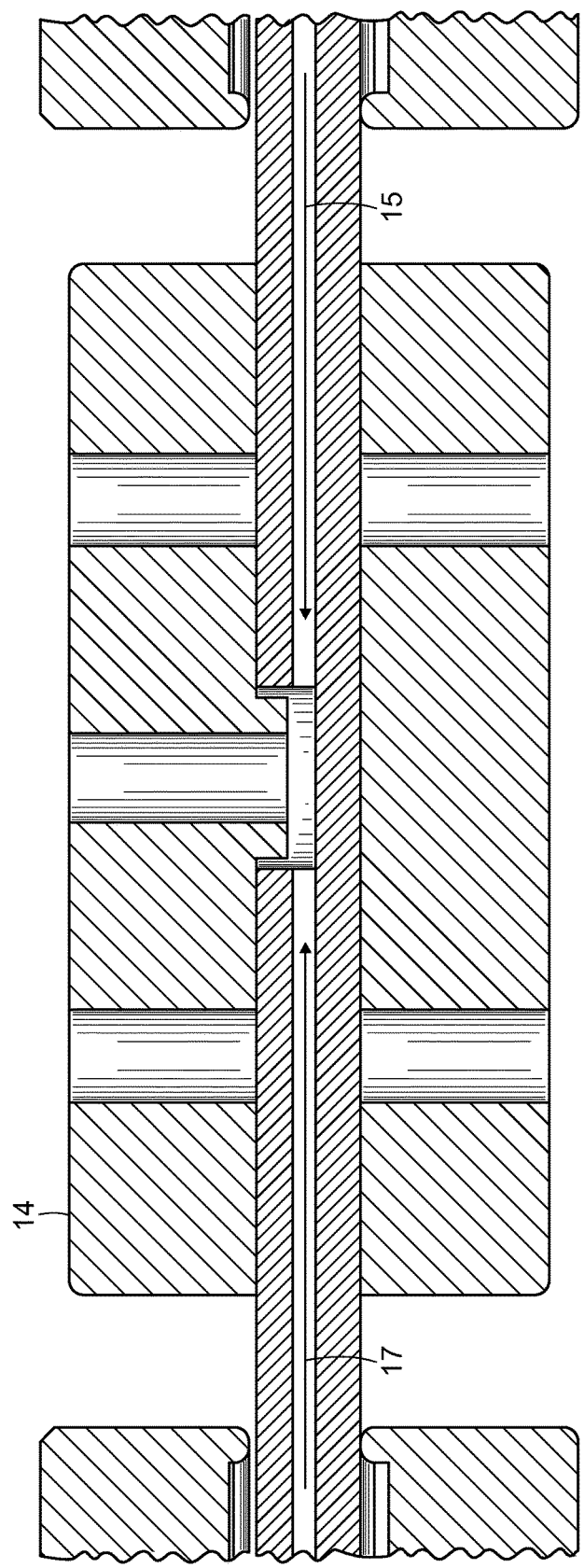
FIGS. 10 and 11 are another embodiment of the present disclosure showing the microfluidic counter-current FID described in Example 3 having either a single exhaust port (FIG. 10) or dual exhaust ports (FIG. 11).
Figure 11:
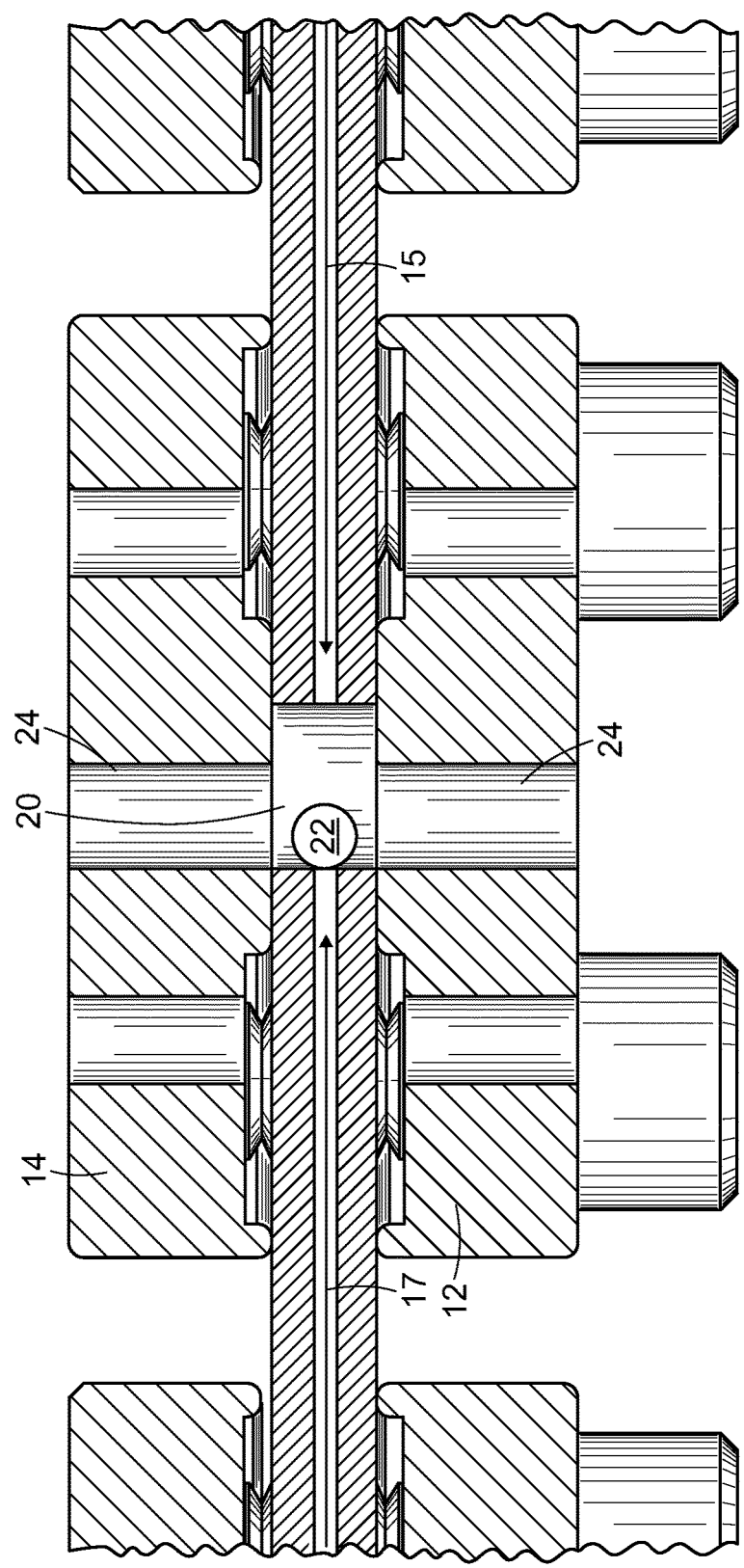

The detector has three ports, one for the column effluent (48) (e.g., from a microfluidic or conventional column), one for hydrogen (46) and one for the oxidant (44). The internal gas channels (15, 17) have cross sectional areas equivalent to a 100 micrometer inner diameter cylinder. The thickness of the device (i.e., the gap between the electrode fittings which cap the ends of the combustion chamber) can be adjusted to better enclose the flame within the fittings. The detector is sized so the flame is easily lit and remains stable in the combustion chamber. The gas channels are sized to match the column diameter to ensure chromatographic performance. The addition of another exhaust port (24) can also better contain the flame. FIGS. 8 and 11 show a duel exhaust port design. FIG. 10 shows a single exhaust port design. In one embodiment, the duel exhaust design worked better to contain the flame within the combustion chamber.

Figure 12:
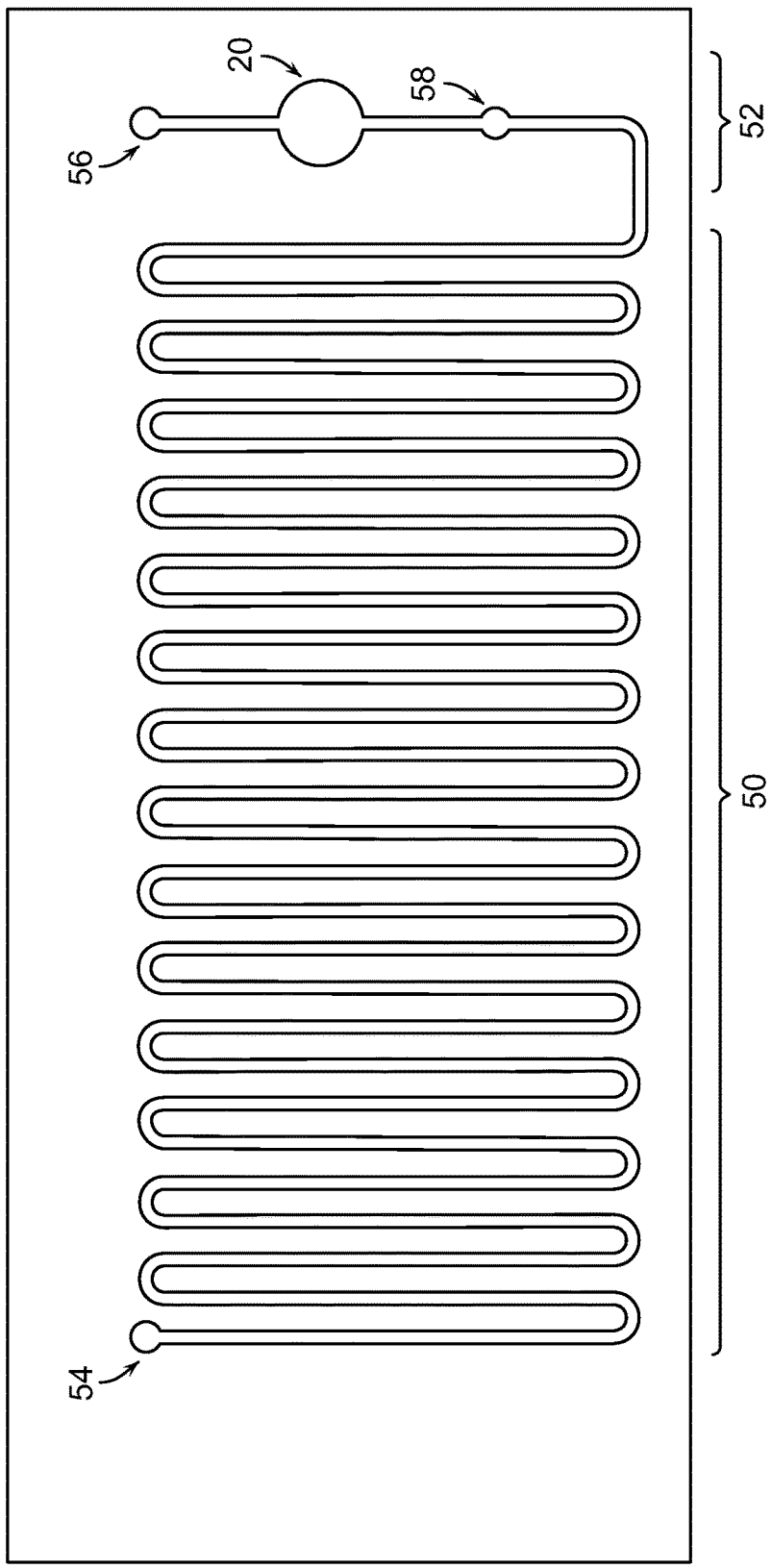
FIG. 12 is another embodiment of the present disclosure showing a microfluidic column integrated with a microfluidic FID.

FIG. 12 shows a microfluidic column (50) integrated with a microfluidic FID (52). In this embodiment, both the column and the FID are on, or in, the same device. The dimensions of the microfluidic FID are about 5 inches by 2.5 inches by about 3 mm thick. The effluent port (48) shown in FIG. 8 can be replaced with the end of the microfluidic column. The column channel is about 5 m long and has a 150 micrometer equivalent cross section. The FID gas channels also had about a 150 micrometer equivalent cross section. The column has a carrier gas port (54) at the head of the microfluidic column and an oxygen gas port (56) and a hydrogen gas port (58) in the FID portion. A sample injector can be incorporated in the carrier gas port. It can also be separate from the carrier gas port (not shown). The sample injector can be one of many commonly available GC samples inlet systems such as split/splitless sample inlet.

While this disclosure has been particularly shown and described with reference to example embodiments thereof, it will be understood by those skilled in the art that various changes in form and details may be made therein without departing from the scope of the invention encompassed by the appended claims.

What is claimed is:

1. A microfluidic flame ionization detector, comprising:
   (i) a housing made of metal, ceramic, polymer, or combinations thereof;
   (ii) a combustion chamber contained within the housing;
   (iii) a microfluidic oxygen inlet contained within the housing and in fluid communication with the combustion chamber;
   (iv) a microfluidic effluent and hydrogen inlet contained within the housing and in fluid communication with the combustion chamber;
   (v) a polarizer electrode; and
   (vi) a collector electrode, wherein the polarizer electrode and collector electrode are electrically isolated from each other at the combustion chamber by an isolator adapted, attached or connected to the housing, wherein the polarizer electrode and the collector electrode provide a potential across the combustion chamber and wherein a portion of the housing functions as at least one of the polarizer electrode or collector electrode.

2. The detector of claim 1, wherein the portion of the housing functions as the polarizer electrode.

3. The detector of claim 1, wherein the portion of the housing functions as the collector electrode.

4. The detector of claim 1, wherein at least two portions of the housing function individually as the polarizer electrode or collector electrode.

5. The detector of claim 1, wherein the oxygen inlet and the effluent and hydrogen inlet are disposed in a non-parallel arrangement relative to one another.

6. The detector of claim 5, wherein the oxygen inlet and the effluent and hydrogen inlet are disposed in a substantially opposing relationship at the combustion chamber.

7. The detector of claim 5, wherein the oxygen inlet and the effluent and hydrogen inlet are disposed at an angle of about 150° to about 210° at the combustion chamber.

8. The detector of claim 1, wherein the portion of the housing comprises ceramic or a polymer.

9. The detector of claim 1, further comprising an exhaust port in fluid communication with the combustion chamber.

10. The detector of claim 1, wherein the polarizer electrode is in communication with a first potential source configured to apply a first potential and the collector electrode is in communication with a second potential source configured to apply a second potential; and the first potential source and the second potential source are configured to have a potential difference between the second potential and the first potential of about 20 V to about 300 V.

11. The detector of claim 1, wherein the polarizer electrode is in communication with a first potential source configured to apply a first potential and the collector electrode is in communication with a second potential source configured to apply a second potential; and the second potential source is configured such that the second potential is a positive potential and the first potential source is configured such that the first potential is a less positive, a negative potential or a neutral potential.

12. The detector of claim 1, wherein the polarizer electrode is in communication with a first potential source configured to apply a first potential and the collector electrode is in communication with a second potential source configured to apply a second potential; and the first potential source is configured such that the first potential is a negative potential and the second potential source is configured such that the second potential is a less negative, a positive potential or a neutral potential.

13. The detector of claim 1, wherein the microfluidic effluent and hydrogen inlet has a cross-sectional area equivalent to an area defined by a round tube having an inner diameter between 40 and 200 μm and supports a hydrogen flow rate through the detector of less than about 100 mL/min.

14. The detector of claim 1, wherein the microfluidic oxygen inlet has a cross-sectional area equivalent to an area defined by a round tube having an inner diameter between 40 and 200 μm and supports an oxygen flow rate through the detector of less than about 100 mL/min.

15. The detector of claim 14, wherein the oxygen source is air and the inlet supports an air flow rate through the detector of less than about 50 mL/min.

16. A microfluidic separation system comprising:
   (i) a sample injector;
   (ii) a separation device in fluid communication and downstream of the injector; and
   (iii) the microfluidic flame ionization detector of claim 1 in fluid communication with and downstream of the separation device.

17. The microfluidic separation system of claim 16, wherein the system is a microfluidic gas chromatographic system or a microfluidic carbon dioxide based chromatographic system.

18. A microfluidic flame ionization detector, comprising:
   (i) a housing made of metal, ceramic, polymer, or combinations thereof;
   (ii) a combustion chamber contained within the housing;
   (iii) a microfluidic oxygen inlet contained within the housing and in fluid communication with the combustion chamber;
   (iv) a microfluidic effluent and hydrogen inlet contained within the housing and in fluid communication with the combustion chamber, wherein the oxygen inlet and the effluent and hydrogen inlet are disposed in a non-parallel arrangement relative to one another;
   (v) a polarizer electrode; and
   (vi) a collector electrode, wherein the second potential is greater than the first potential, wherein the polarizer electrode and collector electrode are electrically isolated from each other at the combustion chamber by an isolator adapted, attached or connected to the housing, wherein the polarizer electrode and collector electrode provide a potential across the combustion chamber, and wherein a portion of the housing functions as at least one of the polarizer electrode or collector electrode.

19. The detector of claim 18, wherein the oxygen inlet and the effluent and hydrogen inlet are disposed in a substantially opposing relationship at the combustion chamber.

20. The detector of claim 18, wherein the oxygen inlet and the effluent and hydrogen inlet are disposed at an angle of about 150° to about 210° at the combustion chamber.

* * * * *